United States Patent [19]

Pile

[11] Patent Number: 4,492,236
[45] Date of Patent: Jan. 8, 1985

[54] APPARATUS FOR BALANCING SKELETAL ALIGNMENT

[76] Inventor: Donald L. Pile, 839 N. Kansas Ave., Topeka, Kans. 66608

[21] Appl. No.: 318,678

[22] Filed: Nov. 5, 1981

[51] Int. Cl.³ .............................................. A61B 5/10
[52] U.S. Cl. .................................. 128/781; 33/174 D
[58] Field of Search ................ 128/69, 781; 33/174 D

[56] References Cited

U.S. PATENT DOCUMENTS

| | | | |
|---|---|---|---|
| 2,535,787 | 12/1950 | Darby | 33/174 D |
| 2,619,729 | 12/1952 | Jarnette | 33/174 D |
| 3,336,917 | 8/1967 | Pile | 128/781 |
| 3,575,159 | 4/1971 | Pile | 33/174 D |
| 3,659,594 | 5/1972 | Schwab | 128/69 |
| 4,033,329 | 7/1977 | Gregory et al. | 128/781 |
| 4,036,213 | 7/1977 | Gregory | 128/781 |

*Primary Examiner*—John D. Yasko
*Assistant Examiner*—C. W. Shedd
*Attorney, Agent, or Firm*—D. A. N. Chase; Michael Yakimo, Jr.

[57] ABSTRACT

A chiropractic apparatus employs first and second measuring devices to determine the amount of anterior/posterior, superior/inferior and lateral displacement of selected skeletal features, particularly the ilia notches, from predetermined reference positions. A patient support assembly employs left and right sole and heel pedal plates rotatable about lateral and longitudinal axes, which allow the operator to position the patient, so as to negate any measured deviations of the skeletal features from the predetermined reference position. A separate upper body alignment device utilizes an overhead target which displays thereon preferred and actual intersections of the major vertical axis running through the skeletal frame of the patient with the pedal plates operated to further position so as to bring the axes into correspondence. Inclination of each pedal plate from the horizontal is read from universal readout gauges which provide data utilized in the construction of heel and sole wedges for insertion into the shoes of the patient. Accordingly, a proper overall position of the skeletal frame is achieved and maintained.

21 Claims, 16 Drawing Figures

APPARATUS FOR BALANCING SKELETAL ALIGNMENT

BACKGROUND OF THE INVENTION

This invention relates to apparatus for use in the proper alignment of skeletal features of a human patient, and more particularly to apparatus for properly aligning the selected skeletal features of the patient in lateral, longitudinal and vertical axes passing therethrough.

Medical professionals, especially chiropractors, are interested in ascertaining the skeletal position of a patient, particularly that of the entire skeletal frame, so that arch pads and/or heel lifts may be utilized in the shoes of the patient to correct malpositioned bone structure and thus properly align the skeletal frame. One form of a device addressing such a function is shown in my U.S. Pat. No. 3,336,917 entitled "APPARATUS FOR DETERMINING BONE STRUCTURE MISALIGNMENT" which issued Aug. 22, 1967 and is hereby incorporated by reference herein. Therein I disclosed a therapeutic apparatus utilizing laterally spaced-apart measuring arms contacting the laterally spaced-apart notches as located below the anterior superior crest of the ilia. These measuring arms have readout gauges associated therewith for indicating the degree of relative anterior/posterior or superior/inferior displacements, if any, between the two notches. If not properly aligned, the patient was moved vertically and/or horizontally relative to and along a base platform until these notches were indicated as being at proper, predetermined alignment. Measurement devices set forth the degree of vertical and/or horizontal movement of the patient from the reference platform plane which is then translated into proper configurations for the heel lifts and/or arch pads.

Although this apparatus was effective in use, I have invented a novel improved apparatus which enables the medical professional to easily ascertain the relative position of selected skeletal features including these iliac notches in anterior/posterior, superior/inferior and lateral directions. In association with these measured displacements and in response to the added lateral determination, I have invented a novel patient support platform device enabling the medical professional to easily adjust the overall attitude of the patient in relation to a referenced horizontal plane so as to move the selected skeletal features into a position negating the presence of the three mesured displacements. Furthermore, I present a new alignment device which enables the medical professional to properly align the head and upper body of the patient, relative to a preferred vertical axis passing therethrough, which can be used to supplement the above discussed skeletal feature alignment so as to more perfectly align the entire skeletal frame.

It is therefore a general object of this invention to provide therapeutic apparatus for properly aligning, with a predetermined reference(s), selected skeletal features of a patient under treatment.

Another object of this invention is to provide apparatus, as aforesaid, allowing for said alignment to correct superior/inferior, posterior/anterior and lateral displacements of said skeletal features from corresponding predetermined references.

Still another object of this invention is to provide apparatus as aforesaid, which selectably adjusts the position of the patient under treatment, relative to a referenced plane, in a manner to correct any displacement of the skeletal features of the patient from said predetermined references.

It is another object of this invention to provide apparatus, as aforesaid, which has measuring devices for contacting the selected skeletal features of the patient in a manner to determine the presence of said displacements.

Still another object of this invention is to provide apparatus, as aforesaid, in which the measuring devices contact the hip regions of the patients, including the notches below the anterior superior crest of the ilia to determine whether any superior/inferior, posterior/anterior and lateral displacements from predetermined references exist.

A still further object of this invention is to provide a patient support assembly for receiving the patient in a standing position thereon which is operator adjustable along longitudinal and lateral axes so as to move said patient into a position in which no measured displacements exist and thus position the skeletal features of the patient according to the predetermined references.

Still a further object of this invention is to provide a patient support assembly, as aforesaid, having left and right pedal plates therein which are operator adjustable along longitudinal and lateral axes passing therethrough, whereby to concurrently position said patient.

A particular object of this invention is to provide a hydraulic support assembly for each of said pedal plates, including the heel and sole components therein.

Still another general object of this invention is to provide a separate alignment device complimenting the apparatus, as aforesaid, for ascertaining the attitude of a selected vertical axis passing through the skeletal frame of the patient.

A more particular object of this invention is to provide the vertical axis alignment device, as aforesaid, which ascertains the proper attitude of the spinal column of the patient relative to a predetermined reference.

Still a further object of this invention is to provide a vertical axis alignment device, as aforesaid, having display means incorporated therein which indicates the preferred and actual attitudes of the selected vertical axis of the patient.

Another particular object of this invention is to provide a vertical axis alignment device, as aforesaid, which has means therein linking movement of the vertical axis of the patient to movement of the display of the actual attitude of the vertical axis allowing the patient to be moved to a position of correspondence of said axis displays.

Other objects and advantages of this invention will become apparent from the following description taken in connection with the accompanying drawings, wherein is set forth by way of illustration and example, an embodiment of this invention.

DESCRIPTION OF THE PREFERRED EMBODIMENT

Figure 1:
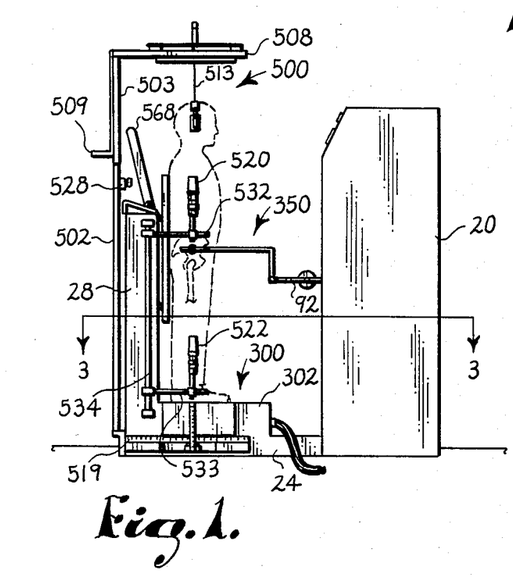
FIG. 1 is a side elevation view of the apparatus with the patient shown in phantom in a standing position therein.
Figure 2:
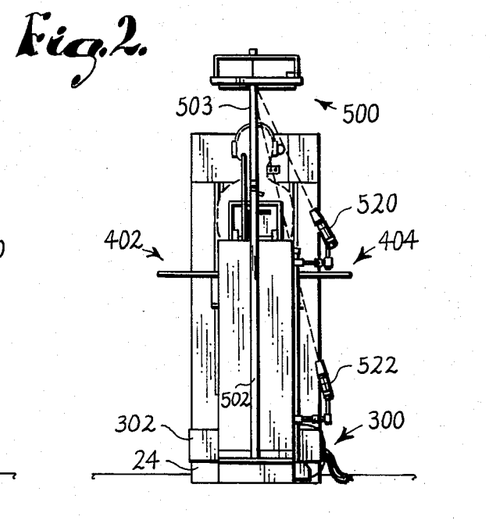
FIG. 2 is a rear elevation view of the apparatus of FIG. 1.

Referring more particularly to the drawings, FIG. 1 shows the apparatus as comprising a housing 20, a hydraulic patient support platform 300, first and second measuring devices 350 and 400 and a superior skeletal alignment assembly 500.

The general apparatus is as set forth in my earlier referenced patent and generally comprises a main console unit 20, a horizontal patient receiving platform 24 having a secondary console 28 being in a longitudinally-spaced apart relationship relative to the main console.

Figures 3, 4:
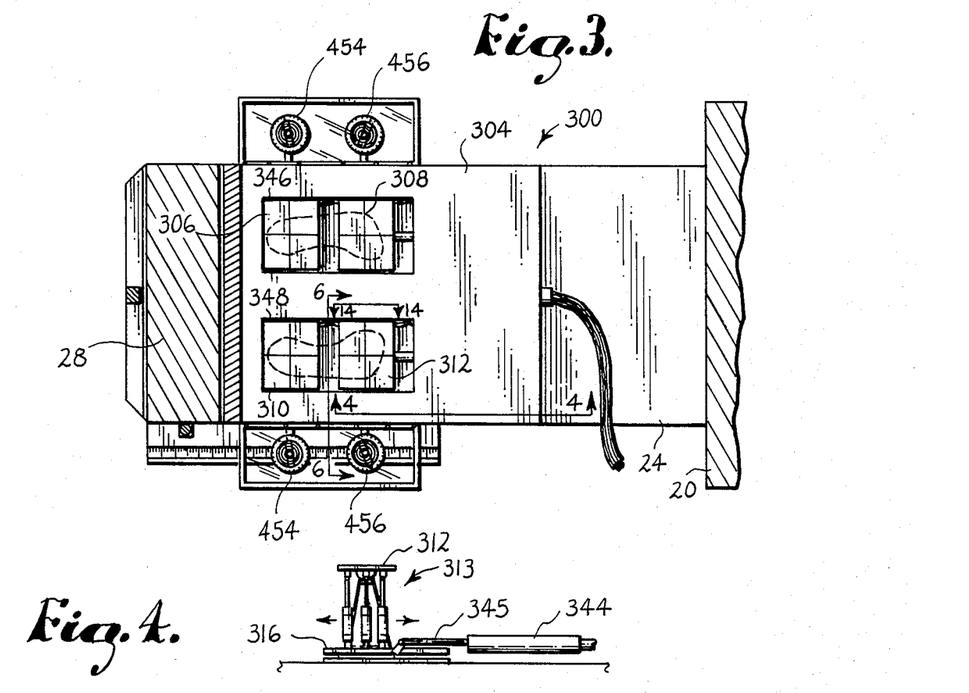
FIG. 3 is a top fragmentary view, on an enlarged scale, showing the heel and sole pedal plates of the patient support assembly and the readout gauges associated therewith.
FIG. 4 is a fragmentary side elevation view, on a reduced scale, showing the means for longitudinally positioning the sole pedal plates of the patient support assembly.

The hydraulic patient support platform assembly 300 is a detachable unit positioned atop the horizontal patient-receiving platform 24. The housing 302 has slots 346, 348 in the planar top wall 304 with a left heel 306 and sole 308 pedal support plates and right heel 310 and sole pedal support plates 312 positioned therein.

Figures 5, 6, 7, 8:
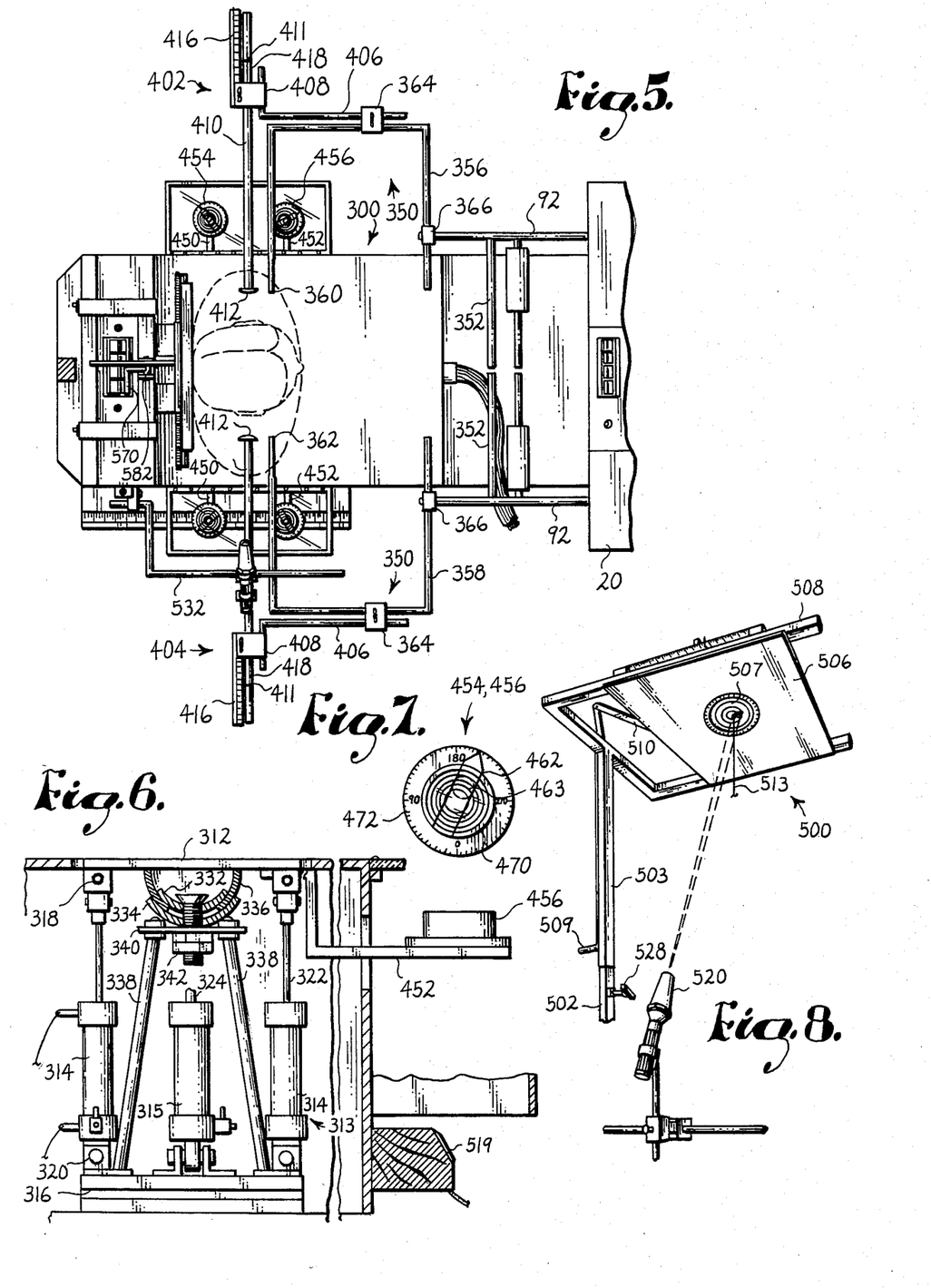
FIG. 5 is a top fragmentary view of the apparatus of FIG. 1, on an enlarged scale, showing the measuring devices and posterior support assembly in contact with the patient.
FIG. 6 is a sectional elevation view, taken along line 6—6 in FIG. 3 and on an enlarged scale, showing the lateral cylinders of the hydraulic support assembly of the right sole pedal plate with one of the longitudinal hydraulic cylinders broken away for purposes of illustration.
FIG. 7 is a top planar view showing the face of one of the readout bubble levels.
FIG. 8 is a partial perspective view of an upper body alignment device, taken from the underside thereof, including the flashlight device for displaying the intersection of the vertical skeletal axis with the target device thereabove.
Figure 14:
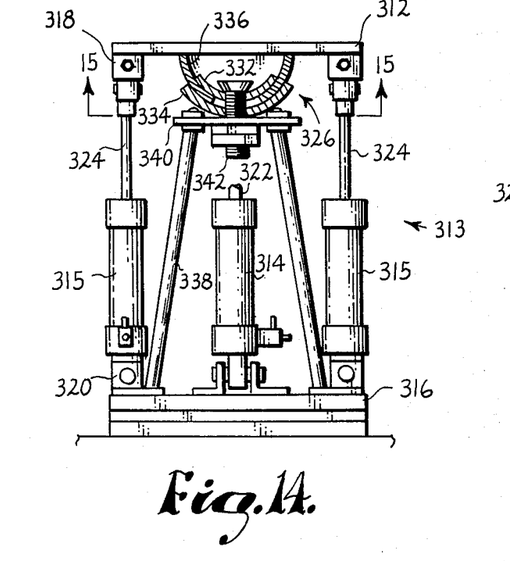
FIG. 14 is a sectional elevation view taken along line 14—14 in FIG. 3 and on an enlarged scale and showing the longitudinal cylinders of the hydraulic support assembly with one of the lateral cylinders being broken away for purposes of illustration.

Offering underlying support to each heel support plate 306, 310 and sole support plate 308, 312 are hydraulic support assemblies, generally designated as 313. Each assembly 313 is as shown in FIGS. 6 and 14 and comprises a pair of laterally spaced-apart hydraulic cylinders 314 and longitudinally spaced-apart hydraulic cylinders 315. As shown, each of the cylinders 314, 315 are connected between a base plate 316 and the sole plate 312 by means of upper 318 and lower 320 brackets. The paired cylinders 314, 315 are in reverse fluid communication so that reverse action of the associated piston rods 322 and 324 of each cylinder pair is provided.

Figure 15:
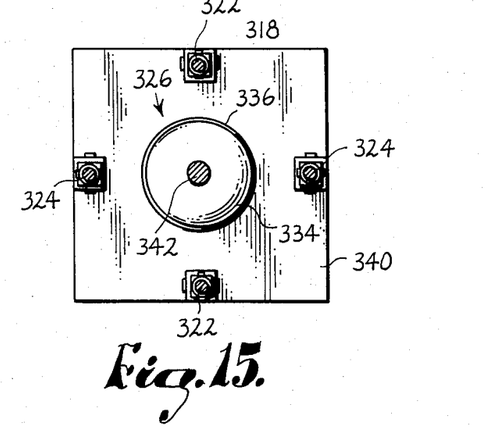
FIG. 15 is a planar view, taken along line 15—15 in FIG. 14, showing the ball joint assembly from the underside thereof.

Centrally mounted to the sole plate 312 is a semispherical ball joint assembly 326 comprising a pair of axially spaced-apart and fixed semispherical half ball plates 332 and 334 which presents a race for insertion of a movable semispherical ball plate 336 therebetween. The ball plate assembly 326 is mounted to a support plate 340 by means of a bolt/nut 342 combination with the support plate 340 held above the base plate 316 by a plurality of leg members 338 attached thereto.

The movable ball plate 336 has a larger hole in the center thereof allowing for movement between ball plates 332 and 334, the bolt 342 acting as a stop pin limiting such movement therebetween.

Although only one hydraulic assembly associated with sole plate 312 has been shown and described, it is understood that each hydraulic assembly 313 associated with the other sole 308 and heel plates 306, 310 are identical in construction. Furthermore, as shown in FIG. 4, the sole plates 308 and 312 are longitudinally adjustable along slots 346, 348 as provided by a longitudinally extending hydraulic cylinder 344 attahed between the main console 20 and the base plate 316 of each sole plate hydraulic elevation assembly. The cylinders 344 with operating piston 345 therein are operator-controlled by a hydraulic power system, not shown, and are thus longitudinally extensible which provides concurrent movement to the hydraulic assembly 313 and respective sole plate 308, 312 connected thereto.

As diagrammatically shown in FIG. 16, as to be subsequently described, fluid communication to the paired cylinders 314, 315 or each hydraulic assembly 313 is operator-controlled so as to selectively extend/retract the piston rods 322 or 324 of each cylinder pair causing movement of the associated pedal plate as supported by the ball joint assembly 326. Thus, an operator controlled tilting of each pedal plate 306, 308, 310, 312 about perpendicular longitudinal and lateral axes passing therethrough is provided.

Figures 11, 12, 13:
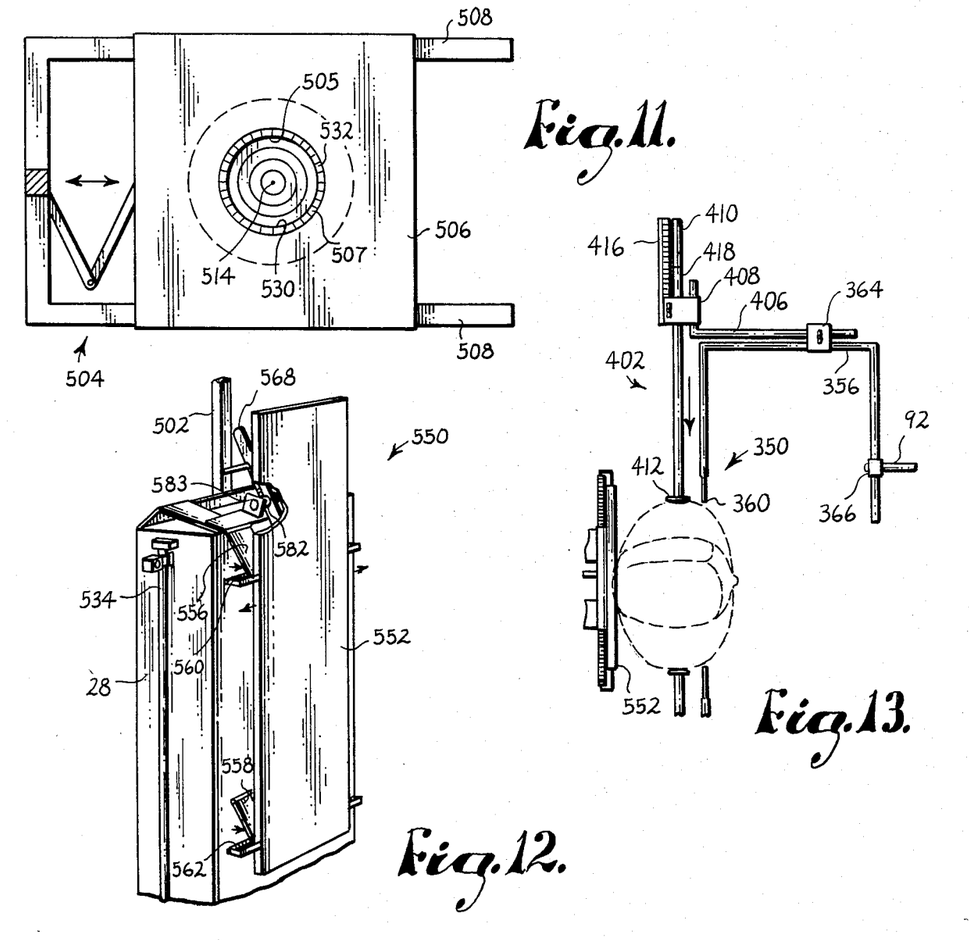
FIG. 11 is a planar view of the target board from the underside thereof.
FIG. 12 is a partial perspective view, showing the posterior support assembly with a portion of the back pad broken away to show the operating lever assembly associated therewith.
FIG. 13 is a partial top view showing the positioning of the patient contact tips of the measuring device and contact ends of the lateral measuring arms immediately prior to contact with the ilia and femur of the posteriorly supported patient.

The interior mechanism of the main console 20 is as described in my earlier referenced patent. Thus, a pair of laterally spaced-apart, horizontally reciprocal and vertically movable arm bars 92 extendible from and movable along slots in the main console 20 is provided. Attached to the end of each bar 92 by bracket 366 is a first measuring device 350 for determining the anterior/posterior and superior/inferior displacement of selected skeletal features of the patient. The device 350 includes a pair of U-shaped measuring arms 356, 358 having patient contact tips 360, 362 thereon. Extending between the bars 92 are a pair of alignment rods 352 acting as finger members pointing one towards the other. These members 352 are in concurrent relative movement with contact tips 360, 362 and provide a visual gauge of the relative positioning of the tips 360, 362.

Further attached to each measuring arm 356, 358 by means of clamps 364 are first and second lateral measuring devices 402, 404. Each assembly generally comprises an L-shaped mounting bar 406 with clamp 408 attached thereto. Attached to each clamp 408 is a sleeve member 418 which slidably receives a laterally extending measuring arm or rod 410 therethrough with a patient contact padded end 412 at the interior end thereof. Each rod 410 has a visual mark 411 thereon for use with an adjacent rule 416 having incremental indicia thereon. The relative degree of lateral displacement of each rod 410 from a predetermined base reference can thus be determined. Although not shown, the rods 410 are spring loaded so as to press firmly against the selected skeletal feature of the patient, the hip region thereof being shown.

Attached to each heel 306, 310 and sole 308, 312 plates in movement therewith are bubble levels 454, 456. Each readout bubble level 454, 456 is fastened to its associated pedal plate by means of stepped mounting brackets 450, 452 allowing for extension of each bubble level 454, 456 to the respective sides of the housing 302. Within each level is a wire arrow 462 presenting a race for movement of the measuring bubble 463 therealong. On the face of each bubble level is a series of concentric rings 470 with movement of the bubble 463 from ring to ring indicating a change in elevation of the level 452, 454 and associated pedal plate 312 from the top wall 304 acting as a horizontal reference plane. About the circumference of each level are circular degree indicia 472 corresponding to the 360 degrees in a circle. In operation each level 454, 456 is rotatable so as to point the arrow to a selected degree. The operator then reads the displacement of the bubble 463 from the center reference ring, if any, at each selected degree position. Accordingly, a 360 degree or universal readout is provided indicating the changes in elevation of the associated pedal plate 306, 308, 310, 312 from the horizontal reference plane. This readout data is translatable to contours in the actual construction of the heel or sole wedges for insertion into the shoes of the patient.

A superiorly positioned skeletal alignment assembly 500 is shown in FIG. 8, 9, 10 and 11 which is designed to properly adjust the attitude of a selected vertical axis extending through the skeletal frame of the patient particularly that axis extending along the spinal column and through the head of the patient. This assembly 500 comprises a vertically extending shaft 502 attached to the bottom of the patient receiving platform 24 receiving the vertical shaft 503 of a U-shaped target frame member 504 slidably mounted thereto to and held in place by locking clamp 528. A target board 506 with target face 507 therein is slidably mounted for longitudinal movement along the laterally spaced arms 508 of the frame 504 such movement being provided by an operator handle 509 connected to scissor hinge 510. The target board 506 has a central aperture 505 surrounded by circular degree indicia 532. A target face 507 is further movable within the target board 506 for registration with the circular aperture 505 as indicated by alignment ring 530 being in correspondence with the edge of aperture 505.

Figures 9, 10:
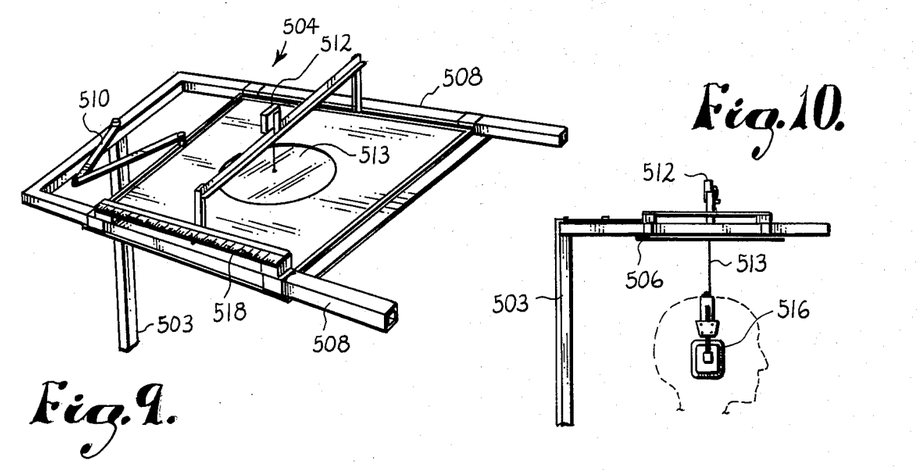
FIG. 9 is a partial perspective view, from the top side thereof, showing the target frame and target device of the apparatus in FIG. 8 slidably mounted thereto.
FIG. 10 is a side elevational view, on a reduced scale, showing the headphones used for linking movement of the head of the patient to movement of the target device.

Attached above the slidable target 507 is a tape measure device 512 having a retractable string 513 therein, the string being fixed to the center 514 of face 507 and passing therethrough for attachment to headphones 516 therebelow. Thus, a linking means is provided between movement of the head of the patient and movement of the target face 507.

A measuring rule 518 indicates the degree of longitudinal displacement of the target board 506 along the frame 504 and is used in coordination with the measuring rule 519 located along the side of the patient-receiving platform 24.

Associated with the assembly 500 is a pair of vertically spaced-apart flashlight devices 520, 522, laterally spaced from the patient. Each flashlight 520, 522 is mounted on an L-shaped arm member 532, 533. Each arm member 532, 533 is slidably connected to a vertical shaft 534 which is fastened to the secondary console 28. Each flashlight 532, 533 is canted relative to the lateral arm member so as to be constructively aligned with the selected vertical axis running through the skeletal frame of the patient. As shown, the selected vertical axis is the major vertical axis extending centrally through the skeletal frame. Accordingly, the flashlight, as canted, is constructively aligned with this central vertical axis and functions in a manner to display a beam of light on the target board 506 so as to show a preferred intersection of this primary vertical axis with the target board 506 thereabove.

As shown in FIGS. 1, 5 and 12, posterior supporting contact of the patient in longitudinal movement along the platform assembly 300 is provided by a back pad assembly 550. This assembly consists of a back pad proper 552 attached to the rear console 28 by upper and lower hinge brackets 556, 558. Extending through each bracket is a spring-loaded rod 560, 562 movable through sleeve bearings 564, 566 which allows lateral movement of the pad 552. The pad 552 is longitudinally adjustable by a lever arm 568 which is rotatably mounted to console 28 by means of a bracket 583 and sleeved 585 axle member 582 passing therethrough. The end of lever arm 568 contacts the upper bracket 556 so that movement of the lever arm 568 about its axle 582 causes the hinge brackets 556 and 558 to swing relative to console 28, which longitudinally moves the back pad 552 into a posterior supporting contact with the patient. A set screw 570 extending through the axle sleeve 585, abuts this axle 582, to prevent movement of the lever arm 582 and thus the corresponding movement of the back pad 552 linked thereto.

Figure 16:
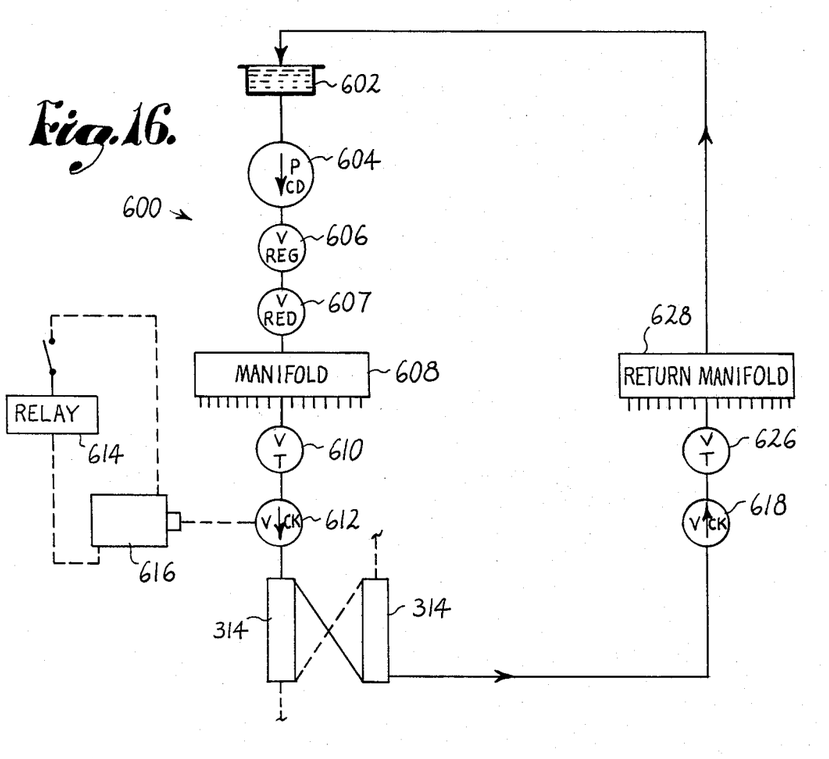
FIG. 16 is a diagrammatic view showing the operator controlled hydraulic power system associated with a pair of hydraulic cylinders of one of the hydraulic support assemblies.

A segment of the hydraulic power system 600 is diagrammatically shown in FIG. 16. It is understood that other hydraulic systems providing for operator regulation of the hydraulic fluid to the cylinders 314, 315 paired in reverse action may also be utilized. The system 600 generally comprises a fluid reservoir 602 from which the fluid is drawn by a pump 604. Valve 606 regulates the fluid from the pump at 500 PSI which is then reduced to 125 PSI by reduction valve 607 before entry into the intake manifold 608. Speed control or throttle valve 610 regulates the fluid discharging from the manifold with a fluid path check valve 612 controlling delivery to the cylinder pair 314. Check valve 612 is operator-controlled by the relay 614/solenoid 616 combination. Upon activation thereof, the fluid flows to a paired cylinder combination 314 for operating the piston rods 322 to provide a desired degree of tilt of the associated pedal plate in one direction about the lateral axis passing between the laterally spaced-apart cylinders 314. A similar flow path for providing operator controlled tilting in the reverse direction is also provided. The return fluid flows through a check valve 618 before passage through a throttle valve 626 and into a return manifold 628 where the fluid is then routed to the fluid reservoir 602.

Each pedal plate will also have the above-described control means to regulate fluid flow to the longitudinally-spaced cylinder pair 315 so as to provide a reversible action of the piston rods 324 therein and thus the desired tilting of the plate about the longitudinal axis passing through the planar surface thereof.

Each cylinder pair 314, 315 of each plate 306, 308, 310, 312 is likewise controlled so as to allow operator regulation of the degree of reversible tilting of each pedal plate about a longitudinal and lateral axis passing therethrough, such axes being perpendicular in my preferred embodiment.

OPERATION

In operation the heel 306, 310 and sole plates 308, 312 are moved to a level position by means of the hydraulic system 600 as indicated by centering of the bubble 463 within the center ring of each respective bubble level 454, 456. The feet of the patient are positioned on the respective pedal plates with the buttocks and back of the patient supported against the back pad 552 as positioned by operation of lever arm 568. The sole plates 308, 312 are longitudinally adjustable by the operator, as provided by actuation of extensible cylinder 344.

For purposes of illustration and not limitation discussion of the alignment of the ilia and upper body of the patient is herein set forth. Accordingly, the arms 92 with attached first measuring devices 350 are positioned by the operator until patient contact tips 360 and 362 are in contact with the respective notches below the anterior/superior crest of the respective ilia. Movement of the bars 92 is provided as described in my former patent, or can be manually adjustable along the slots in the main console 20, both in longitudinal and vertical extension.

Once the tips 360, 362 are brought into precise contact with the notches, the ends of the alignment rods 352 are then visually checked. If the alignment rods 352 are in a proper facing relationship, one pointing towards the other, there is no relative displacement of the ilia notches in the anterior/superior and superior/inferior planes. However, the displacement of these ends 352 from the proper opposing relationship also indicates the displacement between the ilia notches.

Concurrently, the first and second lateral measuring devices 402, 404 are utilized so that the patient contact end 412 of the laterally extending arms 410 are brought into contact with the center hip region of the patient. Inspection of the visual reference mark 411 on each lateral arm 410 in conjunction with the adjacent rule 416 indicates whether there is any relative lateral displacement of this hip area.

If misalignment of the notches is indicated by displacement of the alignment bars 352 or lateral measuring devices 402, 404 the operator tilts the respective pedal plates about their lateral and longitudinal axes until the opposing tips of the alignment bars 352 are brought into their proper opposed relationship and/or until no relative lateral displacement is shown by the visual reference 411/rule 416 combination.

The superior skeletal alignment assembly 500 is then utilized. In this instance, the upper flashlight devices 520 is positioned in a lateral extension from the great trochanter or the lower flashlight 522 in a lateral extension from the ankle, as shown in FIG. 1. The flashlights 520, 522 are selectively canted to present a constructive alignment of the flashlight with the major vertical axis running through the skeletal frame of the patient. It is preferred that the lower flashlight 522 be used as there is less inherent deviation in the skeletal frame of the patient at that position, although the upper flashlight 520 may be used with satisfactory results.

The longitudinal displacement of the ankle of the patient from the shaft 502 is then measured as provided by the lower rule 519. The target board 506 is then moved along the frame 504 by operation of the handle 509 of scissor hinge 510 until a corresponding distance between the center of the central aperture 505 is presented as indicated along rule 518. The headphones 516 are then placed on the head of the patient with the retractable string 513 extending between the headphones and the upper measuring tape device. The string 513 serves as a physical extension of the major vertical axis and is connected to the center of the target face 507 so that movement of the upper body and the head of the patient moves the target face 507 within the target board 506. Thus, the position of the target face displays the actual intersection of the vertical axis with the target board 506.

The flashlight 522 is then turned on with the beam shining on the target area. This beam displays a preferred intersection of the vertical axis with the target board 506. A proper upper body alignment of the patient, as measured along this major vertical axis, is indicated if the target face 507 is registered within the central aperture 505 and the center 514 or bull's-eye target face 507 is in correspondence with the beam of light thereon. Thus, visual displays of the preferred and actual intersection of the major vertical axis and the deviation therebetween are presented on the target board 506.

If no correspondence between the displays of actual and preferred axial intersection is shown, operation of the heel and sole plates provides an attitudinal adjustment of the patient and the measured axis. The target face 507 linked to the patient responds to such patient movement. Thus, the operator aligns the bull's-eye 514 of target face 507 with the fixed beam of light shining onto the target board 506 until correspondence between the displays is shown and thus a proper alignment of the patient relative to the selected major vertical axes.

Once the proper overall alignment is achieved, the individual gauges 454, 456 are read which, as above-described, present a 360 degree or universal readout of the inclination of each associated pedal plate from a horizontal reference position. Passage of the bubble 463 from the central ring to the outer ring indicates changes in elevation from the horizontal reference plane along the 360 directional degrees as indicated by the surrounding circle indicia 472. This data is transferable to the construction of heel or sole wedges for insertion into the shoes of the wearer so as to mirror the proper position of the patient standing in my apparatus.

Although an analog readout is disclosed herein as provided by the bubble gauges 454, 456, it should be appreciated that the relative inclination of the pedal plates with respect to the reference plane may be ascertained by other means and displayed electrically in digital form.

It is to be understood that while certain forms of this invention have been illustrated and described, it is not limited thereto, except in so far as such limitations are included in the following claims.

Having then described the invention, what is claimed as new and desired to be secured by Letters Patent is:

1. An apparatus for skeletal alignment comprising:
    a patient support assembly having left and right pedal plates for respectively receiving a left foot and right foot of a patient to support said patient in a standing position thereon;
    pivot means for mounting said pedal plates in movement about longitudinal and lateral axes passing through each of said plates;
    a first measuring device having first and second patient contact tips for engaging selected skeletal features of said patient;
    means for mounting said first measuring device to said support assembly in longitudinal and vertical movement relative to said support assembly whereby to provide similar movement of said first and second tips into said engagement with said selected skeletal features;
    a lateral measuring device having first and second laterally spaced-apart measuring arms with each arm having a patient contact free end for engaging selected skeletal features of said patient;
    means for mounting said lateral measuring device to said support assembly in lateral movement relative to said patient whereby to provide similar movement of said free ends of each measuring arm into laterally spaced-apart engagement with said selected skeletal features of said patient;
    a first indicator means operably responsive to said movement of said first and second patient contact tips of said first measuring device to gauge the relative degree of vertical and longitudinal displacement of said first and second patient contact tips and said skeletal features contacted thereby from a predetermined position;
    a second indicator means operably responsive to lateral movement of said first and second arms of said lateral measuring device to guage the relative degree of lateral displacement of said patient contact free ends of said lateral measuring arms and said skeletal features contacted thereby from a predetermined position; and
    control means for selectively moving said pedal plates about said respective axes to adjust the attitude of said patient and said selected skeletal features to a position so that said first and second indicator means respectively gauge said respective predetermined positions.

2. The apparatus as claimed in claim 1, wherein each pedal plate comprises:
    a heel plate;
    a sole plate longitudinally spaced from said heel plate; and
    means for adjusting the longitudinal displacement of said sole plate from said heel plate whereby to conform each pedal plate to the foot of the patient.

3. The apparatus as claimed in claims 1 or 2, wherein said pivot means comprises:
    a ball joint assembly mounted to each plate for allowing motion of each plate about said longitudinal and lateral axes passing therethrough;
    a pair of longitudinally spaced-apart hydraulic cylinders, each having an operating piston therein connected to each plate along said longitudinal axis;
    a pair of laterally spaced-apart hydraulic cylinders, each having an operating piston therein connected to each plate along said lateral axis;
    fluid flow means for delivering a hydraulic fluid to each cylinder of each cylinder pair in a manner providing for reverse action of the operating pistons therein; and
    said control means being a hydraulic power system providing for operator regulation of said fluid flow to each cylinder pair whereby to selectively operate said pistons and tilt each plate about said longitudinal or lateral axes.

4. The apparatus as claimed in claims 1 or 2, wherein said pivot means comprises:
    a pair of longitudinally spaced-apart hydraulic cylinders each having an operating piston therein connected to each plate along said longitudinal axis;
    a pair of lateraly spaced-apart hydraulic cylinders each having an operating piston therein connected to each plate along said lateral axis;
    fluid flow means for delivering a hydraulic fluid to each cylinder of each pair of cylinders in a manner providing reverse action of the operating pistons therein, and
    said control means being a hydraulic power system providing for operator regulation of said fluid flow to each cylinder pair, whereby to selectively operate said pistons and tilt each plate about said longitudinal or lateral axes.

5. The apparatus as claimed in claims 1 or 2, wherein is provided means responsive to movement of said plates from a referenced plane for measuring the relative displacement of said plates therefrom, said measured displacement providing data usable for preparation of corrective heel and arch supports for insertion into the shoes of the patient.

6. The apparatus as claimed in claim 5, wherein said measuring means includes:
    a bubble level having a readout face therein;
    a plurality of measuring indicia on said readout face, including a central reference index corresponding to the desired inclination of said referenced plane;
    a pointer on said readout face having structure therein for providing a race for movement of the readout bubble therealong;
    indicia surrounding said readout face corresponding to the 360 degrees in a circle with said central reference index corresponding to the center of said circle;
    means for aligning said bubble level and said pointer with at least one of said selected circle indicia, said bubble being displaced along said race from said central reference point at a distance shown by said measuring indicia, said distance corresponding to a predetermined change in inclination of said associated plate from said referenced plane relative to the direction of said pointer, whereby to provide a plurality of readouts of said inclinations of said plate to present said usable data.

7. The apparatus as claimed in claim 1, wherein said second indicator means comprises:
    a measuring rule associated with each of said measuring arms and having incremental indicia thereon; and
    pointer means on each measuring arm for indicating the degree of lateral displacement of said measuring arm from a referenced indicia on said rule upon said engagement of said free end of each arm with said selected skeletal features.

8. The apparatus as claimed in claim 1, further comprising means for supporting said patient comprising:
   a back pad;
   means for mounting said back pad to said apparatus in a generally parallel position relative to the skeletal frame of said patient; and
   means for positioning said back pad into a posterior supporting contact with the patient standing on said patient support assembly.

9. The apparatus as claimed in claim 8, wherein said pad member mounting means comprises:
   an upstanding support structure positioned to the rear of said apparatus and said patient;
   hinge brackets mounted to said support structure for connecting said pad member to said support structure in a spaced apart displacement therefrom, said hinge brackets swingable in a manner to variously adjust said displacement of said back pad for movement into said supporting contact.

10. The apparatus as claimed in claim 9, wherein said back pad positioning means comprises:
    a lever arm;
    means for rotatably mounting said lever arm to said support structure;
    means connecting said lever arm to a hinge bracket whereby movement of said lever arm swings said hinge bracket and said connected back pad into said posterior supporting contact; and
    locking means for precluding said rotatable lever arm movement for maintaining said back pad in said posteriorly contacting position.

11. The apparatus as claimed in claim 1, wherein said first indicator means comprises:
    first and second finger members;
    means for mounting said first and second finger members to said first measuring device in concurrent movement with said first and second contact tips and in a generally facing relationship therebetween, said facing relationship of said finger members corresponding to the facing relationship of said first and second patient contact tips whereby said relationship of said finger members presents a visual gauge of the relative displacement of said first and second patient contact tips.

12. The apparatus as claimed in claim 1, further comprising a skeletal alignment assembly including:
    a target device;
    means for positioning said target device over the head of said patient;
    a first display means for presenting on said target device an index of the intersection of a generally vertical axis with said target device, said axis passing through the skeleton of said patient in a preferred direction corresponding to a proper alignment of a selected skeletal structure;
    a second display means for presenting on said target device an index of the intersection of a generally vertical axis with said target device, said axis passing through the skeleton of said patient in a direction as actually defined by said selected skeletal structure; and
    said control means operable to adjust the attitude of said skeleton of said patient providing for alignment of said first and second indicia on said target device corresponding to an alignment of said preferred and actual skeletal axes, whereby said selected skeletal structure is properly aligned.

13. The apparatus as claimed in claim 12 wherein said target device comprises:
    a target frame;
    a target board within said target frame; and
    means for supporting said target frame in a position above the head of said patient, said target board receiving said first and second indicia thereon as respectively provided by said first and second display means.

14. The apparatus as claimed in claim 13 wherein said first display means comprises:
    a light source; and
    support means for constructively aligning said light source with said preferred skeletal axis, said light source presenting a beam on said target board to present said first index thereon, whereby alignment of said light source with said second index on said target board corresponds to an alignment of said preferred and actual skeletal axes of said patient.

15. The apparatus as claimed in claim 14, wherein said second display means comprises:
    a target face;
    an aiming point on said target face;
    means for sliding said target face along said target board; and
    means for linking said slidable movement of said target free to movement of said skeletal axis of said patient during said control means adjustment so that said aiming point indicates said intersection of said actual skeletal axis with said target board during movement of said actual skeletal axis, whereby alignment of said aiming point with said beam indicates an alignment of said actual and preferred skeletal axes of said patient.

16. The apparatus claimed as in claim 15, wherein said linking means comprises:
    a rod member having vertically spaced-apart upper and lower ends;
    means for connecting said rod upper end to said target face; and
    means for connecting said rod lower end to said patient with said aiming point positioned normal to an extension of said actual vertical axis of said patient, whereby movement of said vertical axis of said patient moves said aiming point connected thereto.

17. The apparatus as claimed in claim 16, wherein said rod lower end is connected to the head of said patient in a manner to position said aiming point at the intersection of a vertical axis passing through the spinal column of said patient with said preferred axis corresponding to the preferred attitude of said spinal column of said patient whereby said alignment of said indicia on said target properly aligns the head and upper body of said patient.

18. An apparatus for use in the alignment of skeletal features comprising:
    a horizontal platform for receiving a patient in a standing position thereon;
    a first measuring device having first and second patient contact tips for engaging selected skeletal features of said patient;
    means for mounting said first measuring device to said apparatus in longitudinal and vertical movement relative to said support assembly and said patient standing thereon, whereby to provide similar movement of said first and second tips into said contact with said selected skeletal features;

a lateral measuring device having first and second measuring arms each having a free end therein for engaging selected skeletal features of said patient;

means for mounting said lateral measuring device to said apparatus in lateral movement relative to said patient whereby to provide similar movement of said free ends into a laterally spaced apart engagement with said selected skeletal feature of said patient;

a first indicator means responsive to movement of said first measuring device to gauge the relative degree of longitudinal and vertical displacement between said first and second patient contact tips and said skeletal features contacted thereby;

a second indicator means responsive to movement of said lateral measuring device to gauge the relative degree of lateral displacement between said free end of each measuring arm and said skeletal features whereby misalignment of said associated skeletal features is indicated by said measured relative displacements as gauged by said first and second indicator means.

19. Apparatus for aligning the skeletal frame of a patient comprising:

a horizontal platform for receiving a patient in a standing position thereon;

a target device;

means for positioning said target device over the head of said patient;

a first display means including a light source for presenting on said target device a light-induced image of the intersection of a generally vertical axis with said target device, said axis passing through the skeleton of said patient in a preferred direction corresponding to a proper alignment of a selected skeletal structure;

support means for constructively aligning said display means with said preferred axis to present said light-induced image on said target device defining said index of intersection;

a second display means for presenting on said target device an index of the intersection of a generally vertical axis with said target device, said axis passing through the skeleton of said patient in a direction as actually defined by said selected skeletal structure, whereby misalignment of said selected structure of said skeletal frame is indicated by a deviation between said displayed preferred and actual intersections of said imaginary vertical axis on said target device.

20. The apparatus as claimed in claim 19, wherein said horizontal platform comprises:

a patient support assembly having left and right pedal plates for receiving said patient in said standing position thereon;

pivot means for mounting each pedal plate in movement about longitudinal and lateral axes passing therethrough;

operator control means for selectively moving each pedal plate about said longitudinal and/or lateral axes to adjust said imaginary vertical axis of said selected skeletal structure to a position providing for correspondence between said displayed intersections of said preferred and actual axes with said target device whereby to properly position said selected skeletal structure of said patient in a preferred position.

21. In a chirporactic apparatus having at least one measuring device for indicating the displacement of selected skeletal features of a patient from a predetermined position and having a patient-receiving platform for receiving the respective feet of said patient, said platform comprising:

a patient support assembly having complementary left and right heel and sole pedal plates for receiving the heel and sole of said patient in a standing position thereon;

pivot means for mounting each pedal plate in movement about a longitudinal and a lateral axis passing therethrough;

operator control means for selectively moving each heel and sole pedal plate about said longitudinal and lateral axes passing therethrough to any one of a number of positions relative to said axes whereby said pedal plates cooperate to adjust the attitude of said patient and said selected skeletal features to said predetermined position.

* * * * *

UNITED STATES PATENT AND TRADEMARK OFFICE
CERTIFICATE OF CORRECTION

PATENT NO. : 4,492,236
DATED     : January 8, 1985
INVENTOR(S) : Donald L. Pile

It is certified that error appears in the above-identified patent and that said Letters Patent is hereby corrected as shown below:

Column 4, line 37, delete "attahed" and insert
--attached--.

Column 12, line 67, delete "support assembly" and
insert --platform--.

Signed and Sealed this

Thirteenth Day of August 1985

[SEAL]

Attest:

DONALD J. QUIGG

Attesting Officer

Acting Commissioner of Patents and Trademarks